United States Patent
Malashanko

(10) Patent No.: US 7,477,727 B1
(45) Date of Patent: Jan. 13, 2009

(54) DIGITAL X-RAY IMAGE DETECTOR ARRAY

(76) Inventor: Karl Adolf Malashanko, P.O. Box 326, Little Lake, MI (US) 49833

( * ) Notice: Subject to any disclaimer, the term of this patent is extended or adjusted under 35 U.S.C. 154(b) by 68 days.

(21) Appl. No.: 11/654,989

(22) Filed: Jan. 18, 2007

Related U.S. Application Data

(60) Provisional application No. 60/762,582, filed on Jan. 26, 2006.

(51) Int. Cl.
    *H05G 1/64* (2006.01)
(52) U.S. Cl. .................. 378/98.9; 378/98.8; 250/370.09
(58) Field of Classification Search ............... 378/98.8, 378/98.9; 250/370.09
    See application file for complete search history.

(56) References Cited

U.S. PATENT DOCUMENTS

| | | | |
|---|---|---|---|
| 4,742,230 A * | 5/1988 | Kiri ........................... | 378/98.8 |
| 5,444,756 A | 8/1995 | Pai et al. | |
| 5,485,501 A | 1/1996 | Aichinger | |
| 5,723,866 A * | 3/1998 | Hamilton, Jr. .......... | 250/370.09 |
| 5,751,783 A | 5/1998 | Granfors et al. | |
| 5,773,832 A | 6/1998 | Sayed et al. | |
| 6,084,940 A | 7/2000 | Van Asten | |
| 6,198,800 B1 | 3/2001 | Garland et al. | |
| 6,208,710 B1 | 3/2001 | Nagai | |
| 6,243,441 B1 | 6/2001 | Zur | |
| 6,330,302 B1 | 12/2001 | Joosten | |
| 6,404,851 B1 | 6/2002 | Possin et al. | |
| 6,410,898 B2 | 6/2002 | Deucourant et al. | |
| 6,459,765 B1 | 10/2002 | Ganin et al. | |
| 6,516,098 B2 | 2/2003 | Nonaka | |
| 6,643,411 B2 | 11/2003 | Nonaka | |
| 6,847,698 B2 | 1/2005 | Kaifu et al. | |
| 7,130,377 B2 | 10/2006 | Matsuno | |
| 2003/0226973 A1 * | 12/2003 | Beusch ................. | 250/370.09 |
| 2004/0096035 A1 | 5/2004 | Yamazaki et al. | |
| 2004/0179649 A1 | 9/2004 | Yagi | |
| 2005/0018811 A1 | 1/2005 | Bourgoin | |
| 2007/0023668 A1 * | 2/2007 | Dhurjaty et al. ........ | 250/370.09 |

* cited by examiner

*Primary Examiner*—Chih-Cheng G Kao
(74) *Attorney, Agent, or Firm*—Young Basile

(57) ABSTRACT

A method and apparatus for generating a digital X-ray image is disclosed. The method comprises starting an exposure period wherein an array of X-ray receptors are exposed to X-ray radiation, varying the energy of the X-ray radiation during the exposure period and generating a data value for each receptor in the array of X-ray receptors. Each data value corresponds to the time elapsed between the start of the exposure period and the time at which the magnitude of the X-ray radiation incident upon the corresponding receptor passes a reference value. The data values are processed to generate an image. The apparatus includes an X-ray generator, a clock, an array of X-ray receptors, a comparator, a storage medium, and a processor.

14 Claims, 4 Drawing Sheets

DIGITAL X-RAY IMAGE DETECTOR ARRAY

This application is related to, and claims the benefit of priority from, Provisional Application Ser. No. 60/762,582, filed Jan. 26, 2006.

FIELD OF THE INVENTION

The present invention relates to a digital X-ray image detector array, and more particularly, to a digital X-ray image detector array utilizing an increasing X-ray energy output and a solid state X-ray receptor array for use in generating image data based upon time.

BACKGROUND OF THE INVENTION

Digital radiography is a relatively young art. While its advent has created many benefits to radiographic diagnostics, many aspects of the technology stand in need of improvement or refinement.

A cursory review of prior art devices in the field reveals a host of shortcomings. First, prior art devices use a fixed X-ray dose often dependent upon the particular characteristics of the subject being X-rayed. Although digital devices have reduced the cycle time between an unsuccessful radiographic image and a subsequently successful one, most of these digital devices have provided no improvement in the occasional trial and error methodology of achieving satisfactory radiographic images, particularly relating to X-ray dose. Some prior art inventions have attempted to address this long-standing and fundamental shortcoming in the radiographic arts by introducing test receptors or pattern-matching algorithms for improving images that are faulty on the basis of an incorrect X-ray dose. While these inventions do represent improvements in the art, they fail to address the underlying problem of administering an accurate dose of radiation for imaging on the first attempt.

A further shortcoming of solid state digital radiographic devices is that each utilizes a receptor array to generate data based upon stored analog voltage values. These generated voltages are subject to noise, signal attenuation, and excess charge saturation due to overexposure, all of which detract from information gathered from the X-rayed subject. Further, such devices lack software-based means for refining or calibrating the device to suit specific imaging needs, such as mammography.

It is desirable to have a digital radiographic imaging method capable of generating accurate X-ray images without resort to trial and error. It is also desirable to have a digital radiographic imaging method that is capable of being programmed to suit specific radiographic applications.

SUMMARY OF THE INVENTION

The present invention relates to a method and apparatus for generating a digital X-ray image. The method includes starting an exposure period, wherein an array of X-ray receptors are exposed to X-ray radiation. The energy of the X-ray radiation is varied during the exposure period, and a data value is generated for each receptor in the array of X-ray receptors corresponding to the time elapsed between the start of the exposure period and the time at which the magnitude of the X-ray radiation incident upon that receptor passes a reference value. The data values are processed to generate an image. In order to measure the time elapsed when each receptor passes the reference value, a clock may be initialized at the start of the exposure period for generating a time signal, and the time signal may be supplied to an array of counters, wherein each counter is associated with one of the X-ray receptors of the array of X-ray receptors.

The image that is generated may be formed from an array of pixels having a 1:1 correspondence to the array of X-ray receptors. Furthermore, in processing the date values to generate the image, the data values may be associated with a visual color scale, wherein lower data values correspond to darker colors, and higher data values correspond to lighter colors.

The apparatus includes an X-ray generator for generating X-ray radiation having an increasing energy during an exposure period, a clock for producing a time signal corresponding to the length of the exposure, and an array of X-ray receptors, wherein each receptor of the array of X-ray receptors produces an output signal corresponding to the magnitude of X-ray radiation incident upon it. A comparator is operatively associated with each of the X-ray receptors for comparing the output signal to a reference signal. The apparatus further includes a storage medium for recording a plurality of data values, wherein each data value corresponds to an individual receptor of the array of X-ray receptors and represents the value of the time signal when the output signal of the individual receptor exceeds the reference signal. An image is generated from the plurality of data values by a processor.

BRIEF DESCRIPTION OF THE DRAWINGS

The description makes reference to the accompanying drawings wherein.

DESCRIPTION OF THE ILLUSTRATED EMBODIMENT

Figure 1:
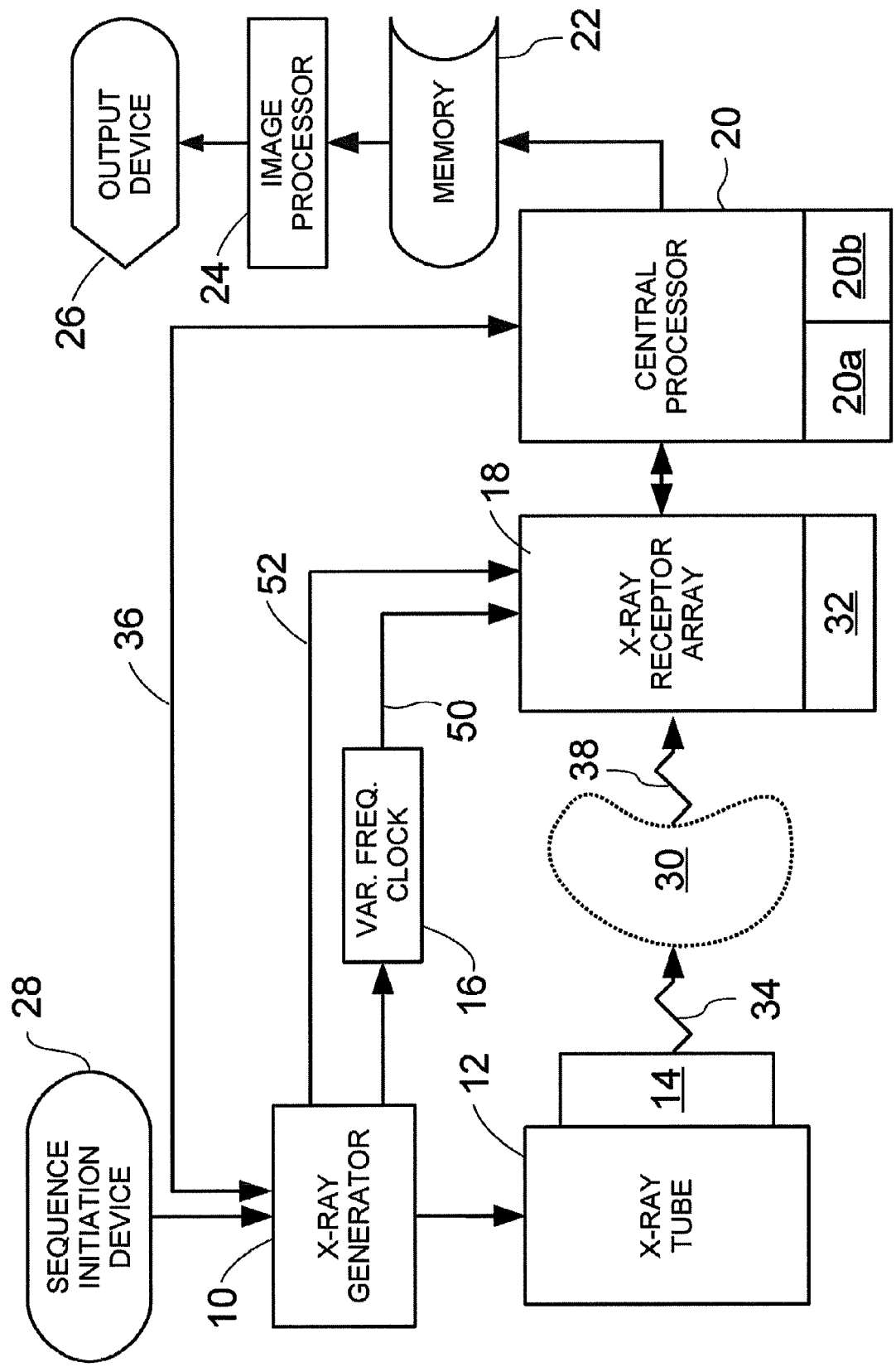
FIG. 1 is a diagram showing a method for generating a digital X-ray image of the present invention.

FIG. 1 depicts a diagram of a method of practicing the present invention. The apparatus components contemplated for use in conjunction with the present invention include an X-ray generator 10, an X-ray tube 12, a collimator 14, a variable frequency clock 16, an X-ray receptor array 18, a central processor 20, an electronic storage or memory device 22, an image processor 24, and an output device 26. Additional items in the diagram include a sequence initiation device 28, a subject of which an X-ray image is desired 30, and a reference voltage 32.

The X-ray generator 10 receives an input signal from the sequence initiation device 28, such as a switch or button, in order to begin the generation of X-rays. The generator 10 drives an X-ray tube 12 to emit X-rays according to a preset energy output profile such as the ones depicted in FIGS. 3 and 4. X-rays emitted by the X-ray tube 12 proceed through the collimator 14 which substantially shapes the X-rays into an X-ray beam 34 to cover a specific area and directs the X-ray beam 34 toward the subject 30 and the X-ray receptor array 18. The X-ray generator 10 also initiates the start of the variable frequency clock 16 to coincide with the commencement of emission of X-rays from the X-ray tube 12.

Figure 3:
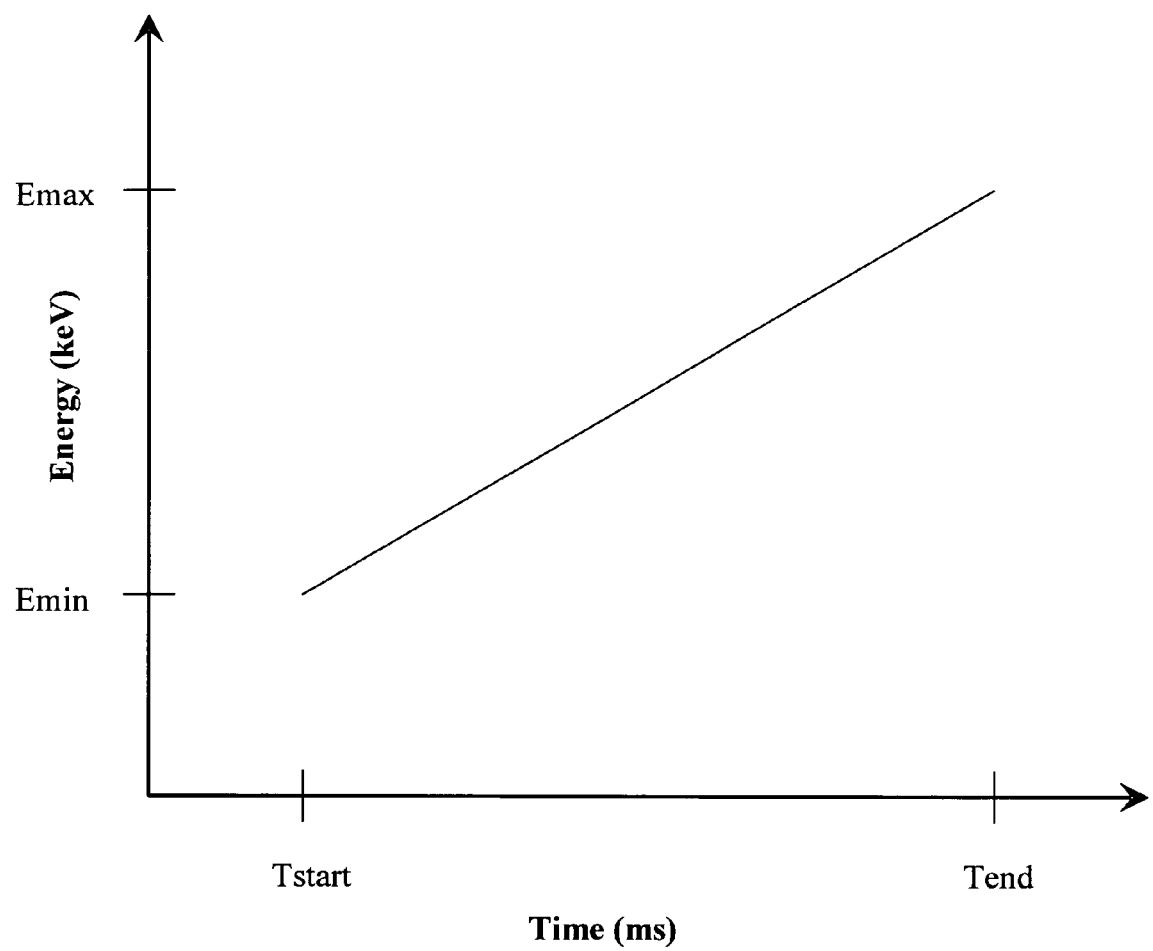
FIG. 3 shows an energy emission profile of an X-ray tube for use in the present invention.
Figure 4:
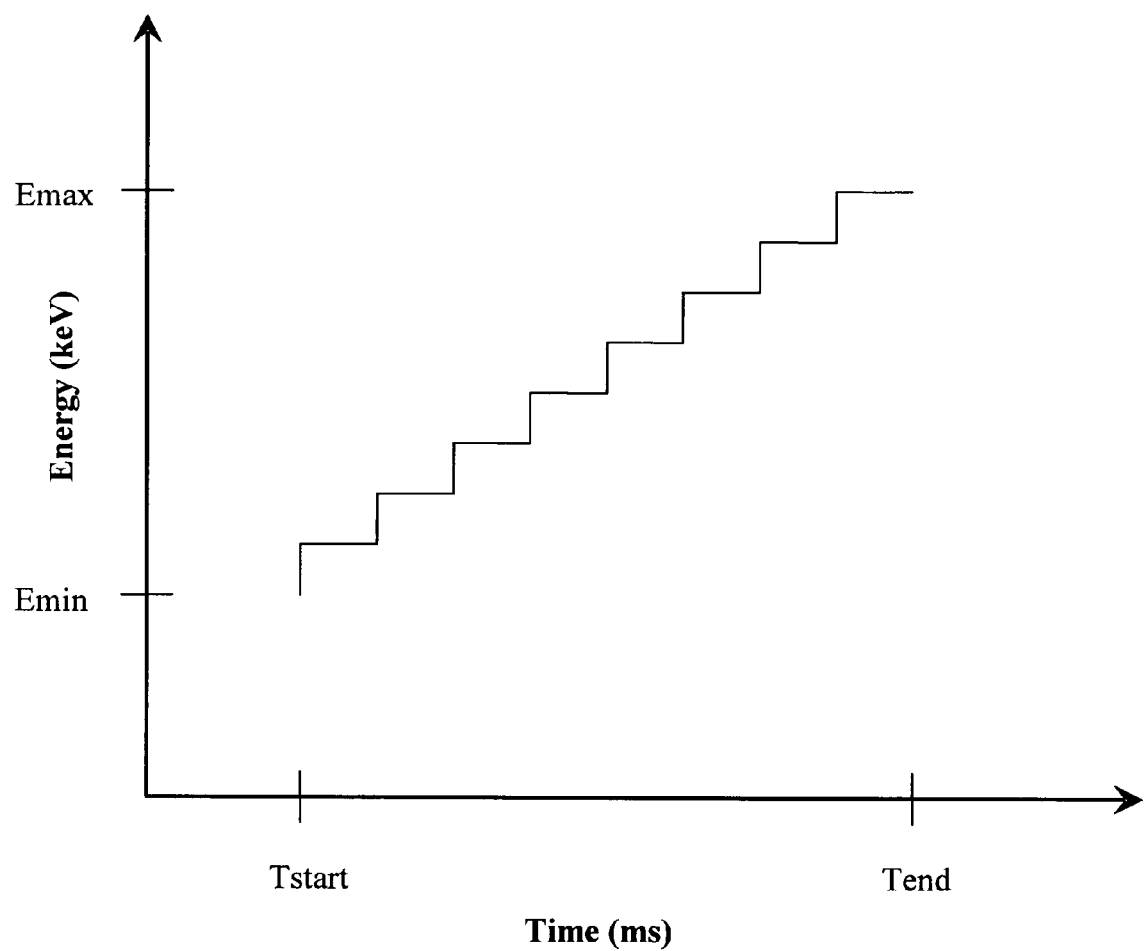
FIG. 4 shows an alternative energy emission profile of an X-ray tube for use in the present invention.

Sample energy profiles of the X-ray beam 34 are depicted in FIGS. 3 and 4. As these figures show, the energy of the X-rays increases over time. The initial time $T_{start}$ corresponds to a relatively low energy state of the X-ray beam 34. The X-ray beam 34 may utilize a variety of profiles having increasing energy, such as linear, stepped, or logarithmic profiles or the like.

The X-ray tube 12 and collimator 14 are oriented so that the X-ray beam 34 emitted by the tube 12 and collimator 14 are directed at the receptor array 18. The tube 12 and collimator 14 are located at a distance spaced apart from the receptor array 18 such that a subject 30 may be interposed in the path of the X-ray beam 34. The subject 30 is typically located immediately adjacent to the receptor array 18.

Figure 2:
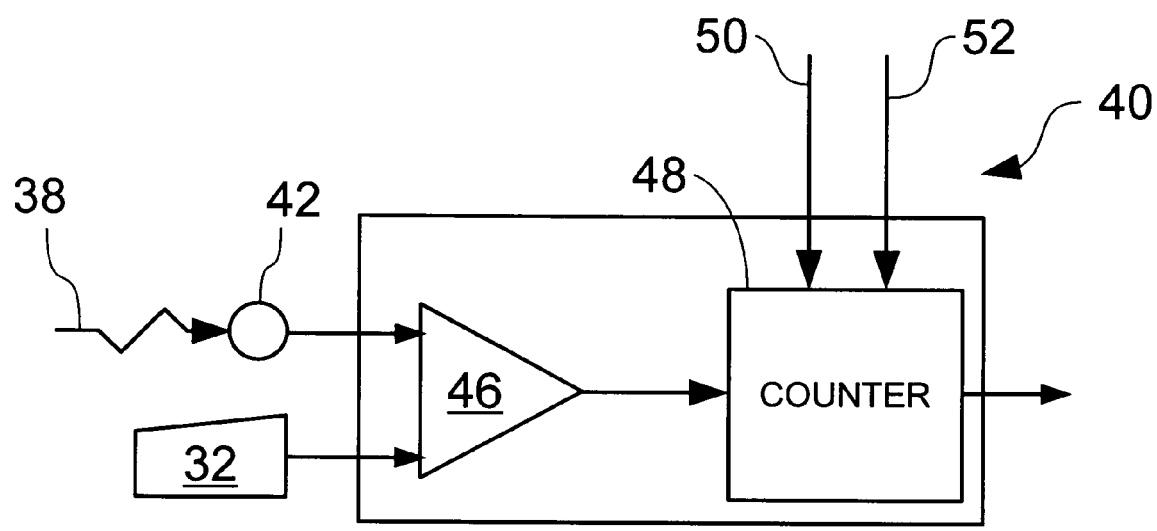
FIG. 2 is a diagram of an individual array element in the X-ray receptor array of the present invention.

The X-ray receptor array 18 is a 2-dimensional array of individual array elements 40. FIG. 2 shows the detail of an individual array element 40. Each array element 40 includes an X-ray sensor or receptor 42. Each X-ray receptor 42 is capable of converting incident X-ray radiation 38 into a corresponding electric potential. The receptors 42 may be arranged in square, rectangular, circular, triangular, or hexagonal patterns within the receptor array 18 and are sufficient in number to provide a resolution appropriate for medical diagnostics. Each receptor 42 may be made from a phosphor or other electron or light-emitting material or a semiconductor material that directly or indirectly generates an electric potential when in the presence of X-ray radiation 38. One or more leads from each receptor 42 is connected to a voltage comparator or threshold detector 46 for that receptor 42 allowing the electric potential of each receptor 42 to be compared against the predetermined reference voltage 32. Each voltage comparator 46 is integral with the X-ray receptor array 18. Each comparator 46 is connected to a counter 48 which receives oscillation pulses 50 from the variable frequency clock 16. When the electric potential of a specific receptor 42 is greater than or equal to the reference voltage 32, the comparator 46 signals the associated counter 48 to cease counting oscillation pulses 50. Thus, each array element 40 converts incident X-ray radiation 38 into an integer number of oscillation pulses 50 that have occurred between the start of the exposure and the instant at which the receptor 42 has reached the reference voltage 32. Overall, the receptor array 18 generates a data array of counter values having a one-to-one correspondence with the receptors 42 that may be output to or through the central processor 20.

The data collected by the X-ray receptor array 18 is communicated to the central processor 20. The central processor 20 has a fixed frequency clock 20*a* and associated microprocessors 20*b*. In the central processor 20, the data collected by the receptor array 18 is converted into image data. When every receptor 42 from the receptor array 18 that has been selected to cover the area of interest has met or exceeded the reference voltage 32, then the central processor 20 generates a signal 36 back to the X-ray generator 10 to cease the generation and emission of the X-ray beam 34. The data is then communicated to the memory or storage device 22. From there, the data is processed by an image processor 24 to a visible image that may be viewed on an output device 26 such as a display screen or a printer device.

In order to provide adequate resolution to an image generated by the system of the present invention, the variable frequency clock 16 changes its frequency according to a predetermined profile at various points during an exposure of the subject 30 to the X-ray beam 34 in order to enhance the differentiation of data points captured by the data array. Alternatively, the energy profile of the X-ray generator 10 as depicted in FIG. 3 or 4 may be modified to any of various non-linear profiles in order to similarly achieve an improved differentiation between data points captured in the receptor array 18.

Turning to FIGS. 3 and 4, energy profiles of the X-ray generator 10 over time are disclosed. The period of time bounded by the starting time, $T_{start}$, and the ending time, $T_{end}$, denotes the exposure time of the digital X-ray method of the present invention. At the beginning of the exposure, the X-ray tube 12 emits X-rays. As the exposure progresses, the X-ray tube 12 emits X-rays having increasing energy states. Once the exposure reaches its ending point, the X-ray generator 10 de-energizes the X-ray tube 12, which ceases its emission of X-rays. In a typical application involving a subject 30 comprising a portion of a human body, the exposure would commence with the emission of X-rays having an energy of approximately 40 keV and proceed up to approximately 150 keV over a total exposure time anywhere from approximately 2 ms to approximately 100 ms. The actual duration of the exposure time is determined by the point at which every receptor 42 in the receptor array 18 has met or exceeded the reference voltage 32 for the exposure. However, it should be understood that the X-ray generator 10 and tube 12 may have such safety features as an absolute time limit for X-ray exposure and an automatic off when the operator releases the initiation device 28, such as an exposure switch or button. These safety features will prevent over-exposing the subject 30 to the X-ray beam 34. The overall exposure parameters will vary based upon the particular subject to be X-rayed. Exposures having significantly higher energy X-rays may be desirable in applications imaging inanimate objects such as metal aircraft parts or shipping containers.

In operation, an operator chooses an appropriate preset energy profile for an exposure based upon the subject 30 to be imaged. Next, the operator aligns the subject 30 such that it is positioned close to the receptor array 18. Finally, the operator initiates the imaging operation by operating the sequence initiation device 28, such as a button or switch.

At the initiation of the imaging operation, the X-ray generator 10 commences a brief warm-up period in order to stabilize the electron emission in the X-ray tube 12. Once the X-ray tube 12 reaches stability and the exposure begins, a signal 52 starts the counter 48 for each receptor 42 in the array 18 and also starts the variable frequency clock 16 at the initial time $T_{start}$. As the X-ray beam 34 emitted from the X-ray tube 12 and collimator 14 encounters the subject 30, the subject 30 causes the X-ray beam 34 to attenuate according to the particular radiographic density of the materials located within the subject 30. The attenuated X-ray radiation 38 then becomes incident on the X-ray receptor array 18. Simultaneously, the clock 16 emits pulses 50 that are counted by each counter 48 in the receptor array 18. As each receptor 42 in the receptor array 18 equals or exceeds the reference voltage 32, the associated comparator 46 signals the associated counter 48 to cease counting oscillation pulses 50. The count values recorded in each counter 48 will vary according to the relative attenuation introduced by the various portions of the particular subject 30. Materials such as bone and other radiographically dense materials will introduce greater attenuation to the incident X-rays 34. The particular receptors 42 in the receptor array 18 located behind such radiographically dense material will require a longer time to achieve the reference voltage 32. Thus, the counter 48 corresponding to the receptor 42 located immediately adjacent to such radiographically dense material will have a correspondingly higher count value. Conversely, lower count values in the receptor array 18 will be associated with radiographically porous materials such as soft human tissue and the like. As described above, once all receptors 42 in the receptor array 18 have equaled or exceeded the reference voltage 32, the central processor 20 sends the signal 36 to the X-ray generator 10 to terminate the X-ray exposure. Once the receptor array 18 has been populated with count values, it will output them to the central processor 20. The data is subsequently communicated to a memory or storage device 22 and processed through the image processor 24 to produce a visual image on an output device 26. Depending upon the particular materials used for the receptor array 18, the entire X-ray imaging system enters a refractory period in which the individual receptors 42 in the receptor array 18 are grounded or otherwise cleared of residual or stored electric potentials. Similarly, the counters 48 in the array 18 are reset during the refractory period.

Due to the variable frequency clock 16, enhanced differentiation can be achieved by increasing the frequency of the variable frequency clock 16 during the exposure. The final X-ray images will display correspondingly finer contrasts to differentiated elements of the subject 30 appearing in the image.

In the course of image processing by the image processor 24, the count values stored as data may be converted to varying colors or shades of gray as desired for a particular application. The data may be manipulated in any appropriate fashion as required by the particular application.

While the present invention has been described in connection with what is presently considered to be the most practical embodiments, it is to be understood that the invention is not limited to those embodiments. To the contrary, the invention is intended to cover various modifications and equivalent arrangements included within the spirit and scope of the appended claims, which scope is to be accorded the broadest interpretation so as to encompass such modifications and equivalent structures as is permitted under the law.

Accordingly, I claim:

1. A method for generating a digital X-ray image, comprising:
    starting an exposure period, wherein an array of X-ray receptors are exposed to X-ray radiation;
    increasing the energy of the X-ray radiation during the exposure period;
    generating a data value for each receptor in the array of X-ray receptors corresponding to the time elapsed between the start of the exposure period and the time at which the magnitude of X-ray radiation incident upon that receptor passes a reference value; and
    processing the data values to generate an image.

2. The method stated in claim 1, further comprising:
    stopping the exposure period when the magnitude of X-ray radiation incident upon all of the receptors of the array of X-ray receptors has passed the reference value.

3. The method stated in claim 1, further comprising:
    initializing a clock at the start of the exposure period for generating a time signal; and
    supplying the time signal to an array of counters, wherein each counter is associated with an X-ray receptor of the array of X-ray receptors for measuring the time elapsed between the start of the exposure period and the time at which the magnitude of X-ray radiation incident upon that receptor passes a reference value.

4. The method stated in claim 3, wherein the time signal is a variable frequency oscillator pulse.

5. The method stated in claim 1, wherein varying the energy of the X-ray radiation further comprises continuously increasing the energy of the x-ray radiation.

6. The method stated in claim 1, wherein processing the data values further comprises associating data values with a visual color scale wherein lower data values correspond with darker colors and higher data values correspond with lighter colors.

7. The method stated in claim 1, wherein the image is formed from an array of pixels having a one-to one correspondence to the array of X-ray receptors.

8. A method for generating a digital X-ray image, comprising:
    generating X-rays having an increasing energy during an exposure period having a starting point;
    initializing a variable frequency clock and an array of counters at the starting point of the exposure period;
    interposing a subject between an emitter of the X-rays and an array of X-ray receptors, wherein the array of receptors has a one-to-one correspondence with the array of counters;
    exposing the array of receptors to collimated X-rays wherein each receptor generates an output signal corresponding to the magnitude of the X-ray radiation incident upon it;
    stopping each of the counters in the array of counters when the output signal of the corresponding X-ray receptor has met or exceeded a predetermined reference signal, thereby defining a counter value for each counter;
    stopping the generation of X-rays when all of the X-ray receptors have met or exceeded the predetermined reference signal;
    recording the counter value from each of the counters in a storage medium; and
    processing the counter values to generate an image of the subject to an output device.

9. The method of claim 8, wherein the processing step further comprises:
    associating counter values with a visual color scale wherein lower counter values correspond with darker colors and higher counter values correspond with lighter colors.

10. The method of claim 8, further comprising:
    each oscillation pulse counter having a one-to-one correspondence with a pixel in the output device.

11. The method of claim 8, further comprising:
    the increasing energy of the collimated X-rays being uniformly linear over time.

12. The method of claim 8, further comprising:
    the increasing energy of the collimated X-rays being stepped over uniform intervals of time.

13. The method stated in claim 8 wherein the output signal is an output voltage and the reference signal is a reference voltage.

14. An apparatus for generating a digital X-ray image, comprising:
    an X-ray generator configured to generate X-ray radiation having an increasing energy during an exposure period;
    a clock configured to produce a time signal corresponding to the length of the exposure period;
    an array of X-ray receptors, wherein each said receptor produces an output signal corresponding to the magnitude of X-ray radiation incident upon it;
    a comparator operatively associated with each said receptor configured to compare said output signal to a reference signal;
    a counter operatively associated with each comparator configured to output a data value;
    a storage medium configured to record the plurality of data values, wherein each said data value corresponds to an individual receptor of said array of X-ray receptors and represents the value of the time signal when said output signal of said individual receptor exceeds said reference signal; and
    a processor configured to generate an image from said plurality of data values.

\* \* \* \* \*